US006059804A

United States Patent [19]

Baer

[11] Patent Number: 6,059,804

[45] Date of Patent: May 9, 2000

[54] PORTABLE DEBEAKING SYSTEM

[76] Inventor: Amos Baer, Rt. 1, Box 76, Lake Park, Minn. 56554

[21] Appl. No.: 09/267,268

[22] Filed: Mar. 12, 1999

[51] Int. Cl.[7] .......... A61B 1/04

[52] U.S. Cl. .......... 606/163; 606/164; 452/166

[58] Field of Search .......... 606/164, 136, 606/163; 452/166; 604/115, 156

[56] References Cited

U.S. PATENT DOCUMENTS

| | | | |
|---|---|---|---|
| 2,385,633 | 9/1945 | Lyon | 606/163 |
| 4,375,814 | 3/1983 | Gourlandt | 606/164 |

*Primary Examiner*—Michael Buiz
*Assistant Examiner*—Len Ngo
*Attorney, Agent, or Firm*—Leo H McCormick, Jr.

[57] ABSTRACT

A portable system moving a debeaker apparatus within a barn to reduce the transportation and handling of a bird. A frame which holds the debeaker apparatus, a receiving chute, a staging cage, a delivery chute and a first and second storage baskets has wheels for easy movement from one location to another location. In a barn, an operator removes a plurality of birds from a starter cage and places the birds in the receiving chute which directs the birds to a platform in the staging cage. The platform has an inclined surface such that the birds have a tendency to face away from the operator. This orientation of the birds assists in the alignment with respect to a head retaining member of the debeaker apparatus. The operator selects a bird from the platform in a staging cage for presentation to the head retaining member associated with the debeaker apparatus. Once a bird is accepted by the head retaining member, a containment shield is resiliently positioned adjacent opening in the top or the return chute. After the beak of the bird is disabled by the debeaker apparatus, the bird is released from the head retaining member. The containment shield limits the movement of the bird as the bird is presented to the return or delivery chute such that the bird is transported to one of the first and second storage baskets. A first counter connected with a central control for the debeaker apparatus is responsive to operation of the debeaker apparatus for directing a predetermined number of birds to each of the first and second storage baskets. A second counter associated with the central control has a first read out which provides an operator with a total number of the birds debeaked during a fixed time period and a second read out which provides an operator with a serial total of the birds debeaked by the debeaking apparatus.

10 Claims, 3 Drawing Sheets

PORTABLE DEBEAKING SYSTEM

This invention relates to a portable debeaking system for disabling a beak of a bird. The system receives a plurality of birds from a starter cage which are placed in a staging area. An operator selects a bird from the staging area and presents the bird to a debeaking apparatus to remove a predetermined portion of its beak. After disabling of the beak, the debeaking apparatus drops the bird into a chute for delivery to a storage basket. Birds are taken from the storage basket to a growing cage.

BACKGROUND OF THE INVENTION

In a flock of birds, leadership, status and authority is established through a pecking order hierarchy. Unfortunately, when birds are raised in a confined area, it is hard and often impossible for a low order bird to escape from higher order birds in such pecking order and as a final result injury and even death of a bird often occurs. To minimize to effectiveness of a beak, it has become a common practice in the poultry business to disable the beak of a bird through the removal of the tip of the beak to reduce the potential use thereof as a weapon when engaging another bird. This disabling practice often occurs when a birds is from one to twenty-one days old. Birds are transported in baskets from a starter cage to a stationary debeaking apparatus of a type disclosed in U.S. Pat. No. 4,375,814. On arrival at the debeaking apparatus, an operator reaches into the basket and selects a bird for insertion into a head retainer mechanism after which the beak is disabled. On completion of the disabling process, the bird is released into the hand of the operator who thereafter places the bird into a basket for return to a growing cage. On return to the growing cage it is not uncommon for a bird to take from one to two days to fully recover and begin to eat in a manner to gain weight. It is believed that the recovery time in addition to the trauma associated with the debeaking apparatus is compounded by the handling and transportation of the birds to the debeaker apparatus. In an effort to reduce trauma associated with disabling of a beak and associated recovery time, structure as disclosed in U.S. Pat. No. 4,951,610 has been developed to accurately control the removal or disabling of the beak of a bird such that only a portion of the beak of a bird is removed and structure as disclosed in U.S. Pat. No. 5,651,731 has been developed such that only the top half of a beak is removed. Currently available debeaker apparatus adequately provide for the disabling of a beak of a bird but unfortunately do not address the trauma associated with transportation and handling of the bird during such debeaking process.

SUMMARY OF THE INVENTION

A primary object of the present invention is to provide a portable debeaking system for use within a barn to limit the handling and transportation of a bird subjected to a debeaking process.

According to this invention, a frame is provided for holding a debeaking apparatus having an associated retention member for holding a bird. A seat is located on the frame to position an operator adjacent the debeaking apparatus. A orientation cage is attached to the frame and with a receiving chute defines a staging section which holds a plurality of birds obtained from a starter cage. The operator selects a bird from the orientation cage and places the head of the bird in the retention member. Once the retention member receives the bird, a signal from a control center activates the debeaking apparatus which thereafter removes a portion of the beak of the bird. After such removal, the retention member releases the bird for delivery to one of first and second storage baskets positioned on the frame through a delivery or return chute. On release of a bird from the retention member, a containment shield limits the direction of movement of the bird such that a bird is directed into the delivery or return chute. Counter means, responsive to the actuation of the debeaker apparatus, totals the number of birds disabled by operation of the debeaking apparatus. After a predetermined number of birds have been presented to the return or delivery chute, the counter means provides the control center with a signal which activates a driver piston to switch a diverter associated with the delivery chute such that birds are thereafter directed from a first storage basket to a second storage basket. After the predetermined number of birds are presented to the first and second storage baskets, the operator returns the birds to a growing cages which may be in close proximity of the portable debeaking system.

An advantage of this debeaking system resides in the limited number of times that an operator actually touches a bird.

A further advantage of this debeaking system resides in the orientation of birds in a staging cage to initiate alignment with a retention member of a debeaking apparatus.

A still further advantage of this debeaking system resides in a reduction of trauma experienced by a bird caused by transporting of a bird from a starter cage to a growing cage by way of a debeaking apparatus to decrease the recovery time it takes to regain a full feeding program for the bird.

DETAILED DESCRIPTION

Figure 1:
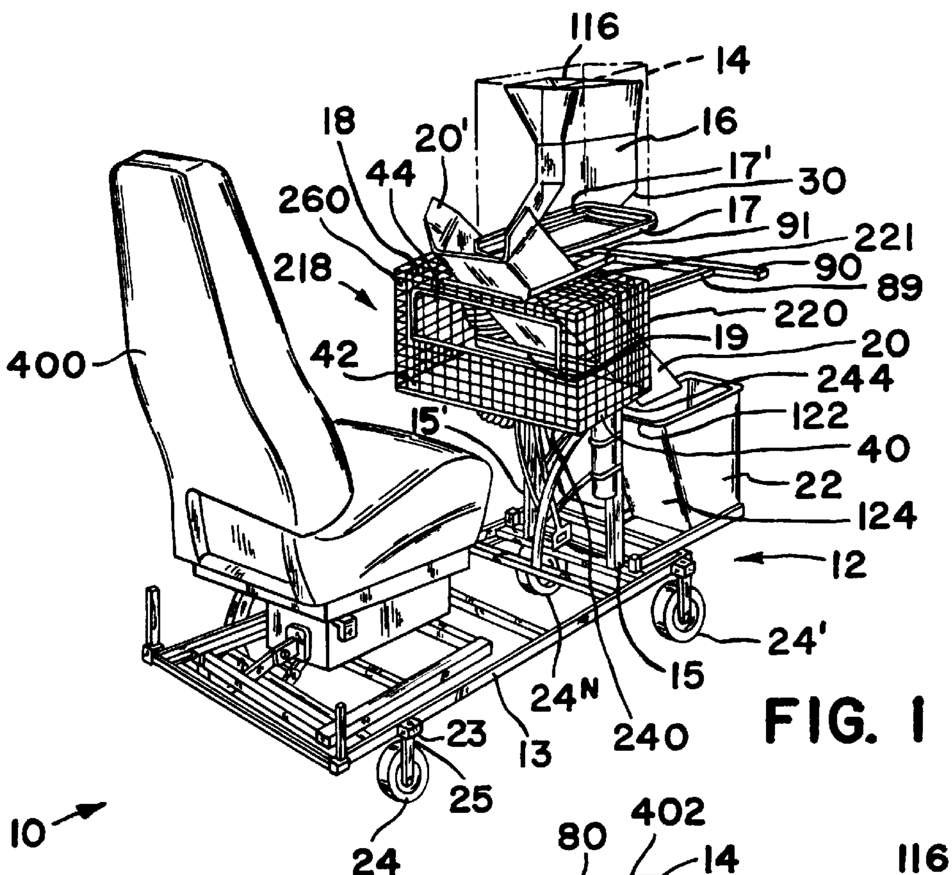
FIG. 1 is a schematic illustration of a system for debeaking a bird in according to the principals of the present invention.

The bebeaking system 10 as shown in FIGS. 1, 2, 3 and 4 includes a truck or frame arrangement 12 which has wheels 24,24', . . . 24" to define a portable arrangement for easily moving a debeaking apparatus 14 of a type fully disclosed in U.S. Pat. No. 4,951,610 and sold by Zootechniques of 78950 Gambais, France under Model No. AG 2000. Through the use of the truck or frame arrangement 12 the debeaking apparatus 14 is brought to birds within a barn rather than transporting birds to a stationary debeaking apparatus.

The truck or frame arrangement 12 has a base 13 with vertical supports 15,15' extending to a predetermined height. First 17 and second 17' horizontal rails are attached to the vertical supports 15,15 to define a shelf or table for receiving the debeaking apparatus 14. The vertical supports 15,15' are tied together by at least one brace member 19 and bar 90 associated with arms 89 and 91 to provide structural rigidity. Vertical supports 15' also provides alignment structure for an enclosed receiving chute 16 and a staging cage 18 of staging means 218 while and vertical supports 15,15' provides alignment structure for debeaker apparatus 14 and delivery chute 20 which returns birds to either a first 22 or second 22' storage baskets from the debeaking apparatus 14.

Wheels 24,24', . . . 24$^n$ are of a type which have a vertical axle retained in a fork 25 held in a bearing member 23 attached to base 13. The bearing member 23 permits a fork 25 to freely rotate in a direction which allows the base 13 to be positioned through the application of force applied by an operator to the hand bar 90. Thus, the truck or frame arrangement 12 may be positioned adjacent a starter cage within a barn and moved along an isles to another starter cage within the barn for a debeaking apparatus 14 to directly receive birds from a starter cage. It being understood that a starter cage is a temporary depository for a large number of birds after hatching which may provide for special accommodations such as temperature control, feeding and humidity for the newly hatched birds. A usual time for retention in a starter cage may be up to three days and thereafter birds are moved to a growing cage having different living conditions such as a smaller number of birds in the same space to accommodate for growth of the birds.

Once an operator positions the truck or frame apparatus 12 adjacent a starter cage, a large quantity of birds are removed from the starter cage and placed in the receiving chute 16 which because of sloped surface 30 causes the birds to slide to a platform 40 in the staging cage 18. The staging cage 18 is designed to hold up to 60 birds and because the platform 40 has an inclined surface 42 essentially all of the birds because of nature, instinctually have a tendency to face up-hill and away from an opening 44 in the front of the staging cage 18. This orientation of the birds makes it easier for a second operator to select a bird for presentation to a head retaining member 50 associated with the debeaking apparatus 14. After a bird is accepted by the head retaining member 50, a containment shield 60 is resiliently positioned adjacent the top of opening 20' of chute 20. When the beak the bird is properly aligned with the debeaking apparatus 14, a starter switch is activated for the control center 402 to operate the debeaking apparatus 14 and whereby a driver mechanism 70 is supplied with pressurized air. The pressurized air moves the driver mechanism 70 correspondingly cutting device 72 to remove a portion of the beak from the bird. Once the portion of the beak has been removed the retaining member 50 releases the bird which falls into return chute 20 for delivery to one of the storage baskets 22,22'. The containment shield 60 limits the movement of the bird on release from retaining member 50 and prevents the bird from attempting to escape out of the top opening 20' of return chute 20. A first counter 80 associated with the operation of the debeaking apparatus 14 and programmed by the operator includes a first indicator 82 which is responsive to the movement of driver piston 70 to provide a cylinder 92 with a signal to direct a diverter gate 94 in the return chute 20 with an input to direct a predetermined number of birds to each of the first 22 and second 22' storage baskets. Once a storage basket 22,22' has received a desired number of debeaked birds, usually between 10–20 birds, the first operator takes such storage basket from truck or frame apparatus 14 and transports the birds to a growing cage. The birds are removed from the storage basket by placing the edge 122 in the growing cage and allowing the birds to slide down the sloped surface 124 without a need for individually handling such birds. Thus, the manual handling by an operator is limited and the transportation trauma experience by a bird during the debeaking process reduced.

In more particular detail, the individual components of this debeaking system are hereinafter described as follows.

The first counter 80, is of a type sold by Red Lion Controls of York, Pa. under Model No. LIBC, and programmed by an operator to provide the control central 402 with a signal whenever the driver piston 70 moves through a predetermine number of cycles of operation. At any time during a debeaking process, the read out of the first counter 80 may be viewed in window 82 by an operator. A number displayed in window 82 provides an operator with the birds in a storage basket currently being filled. The predetermined number of cycles or input to counter 80 can be changed by the operator depending on the desired number of birds which are to be delivered to the storage baskets 22,22' for placement in a growing cage.

Figure 3:
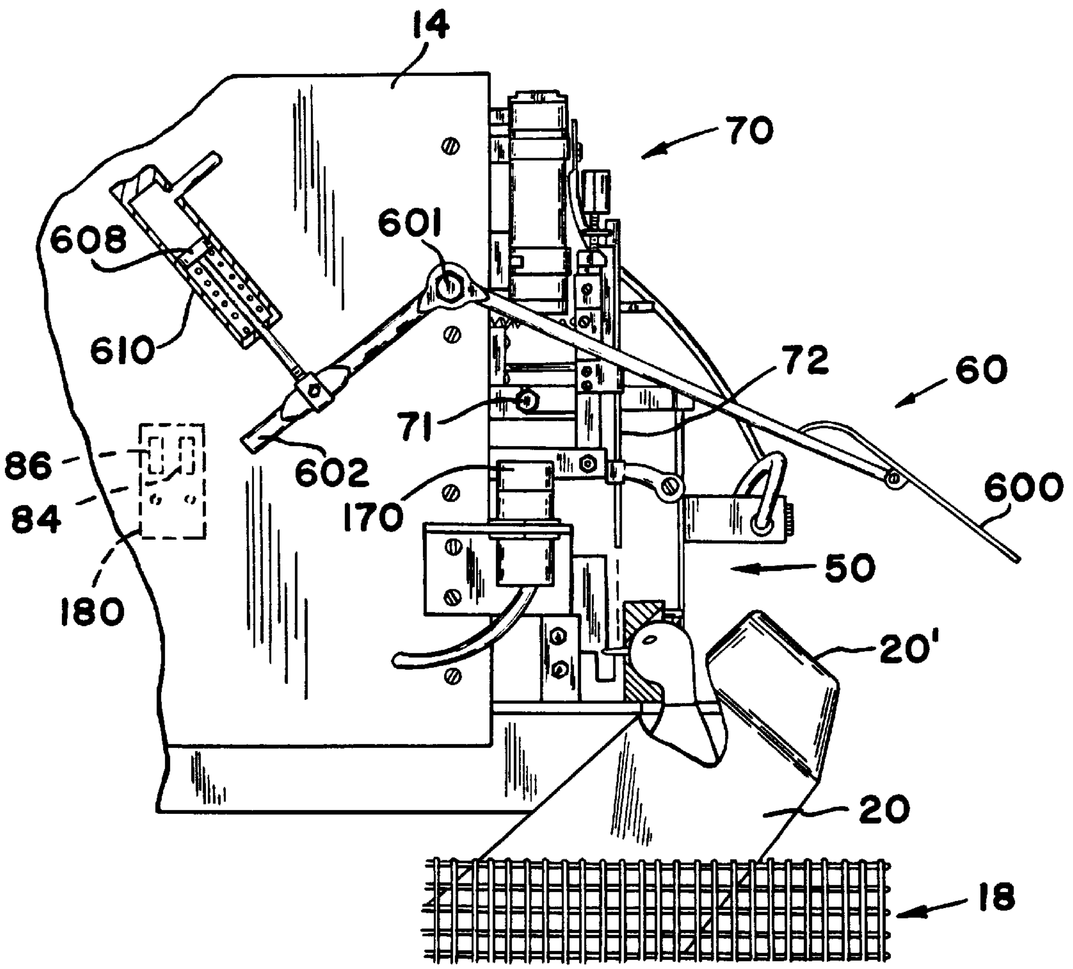
FIG. 3 is a side view of the debeaking apparatus of FIG. 2 illustrating the portion of the debeaking apparatus and a containment member.

A second counter 180, similar to the first counter 80, located on the inside of the housing for the debeaker apparatus 14, see FIG. 3. The second counter 180 is connected to the central control 402 and has a first output indicator 84 which provides a read out to an operator corresponding with a total number of the birds debeaked in a barn during a fixed time period or from a beginning of a starting cage and a second output indicator 86 with a read out to provide an operator with a serial total of the birds debeaked by the debeaking apparatus 14. The first output indicator 84 can be reset by an operator at any time but the second output indicator 86 is fixed and can not be reset.

Figure 4:
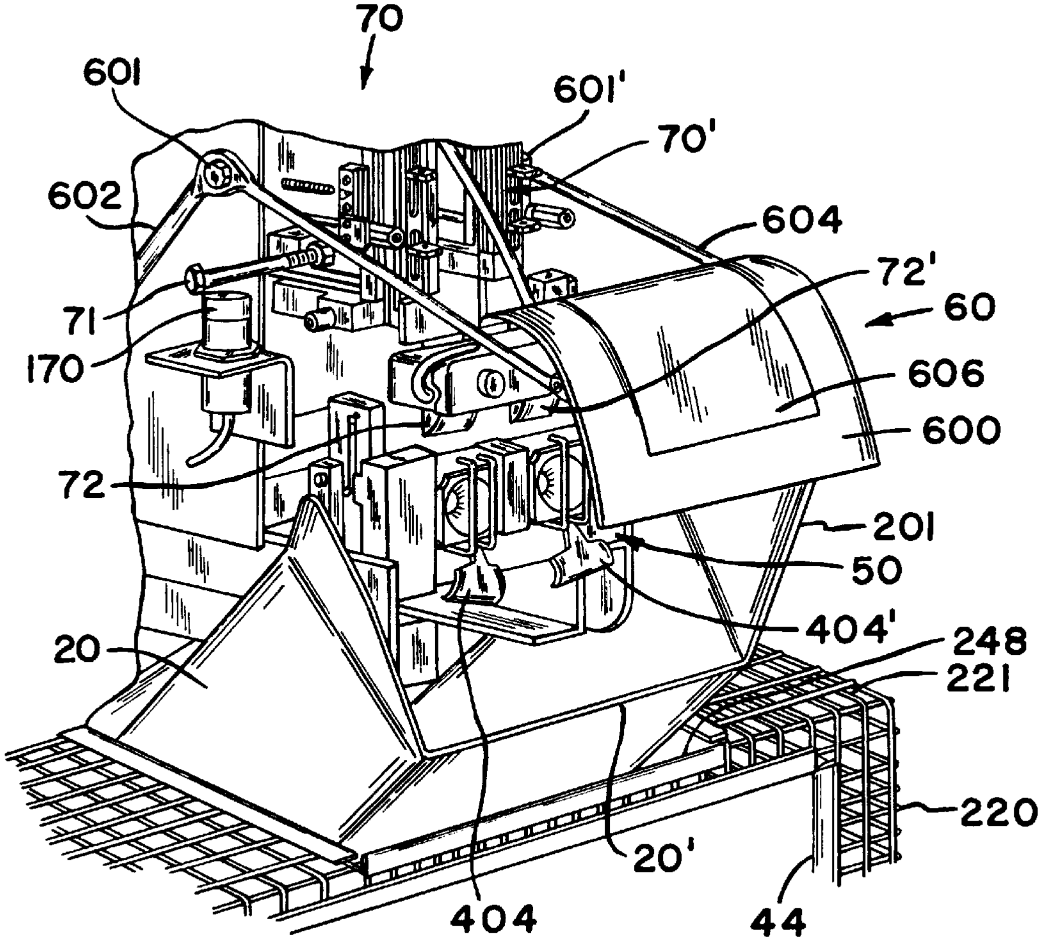
FIG. 4 is a prospective front view of a portion of the debeaking apparatus of FIG. 3.
Figure 5:
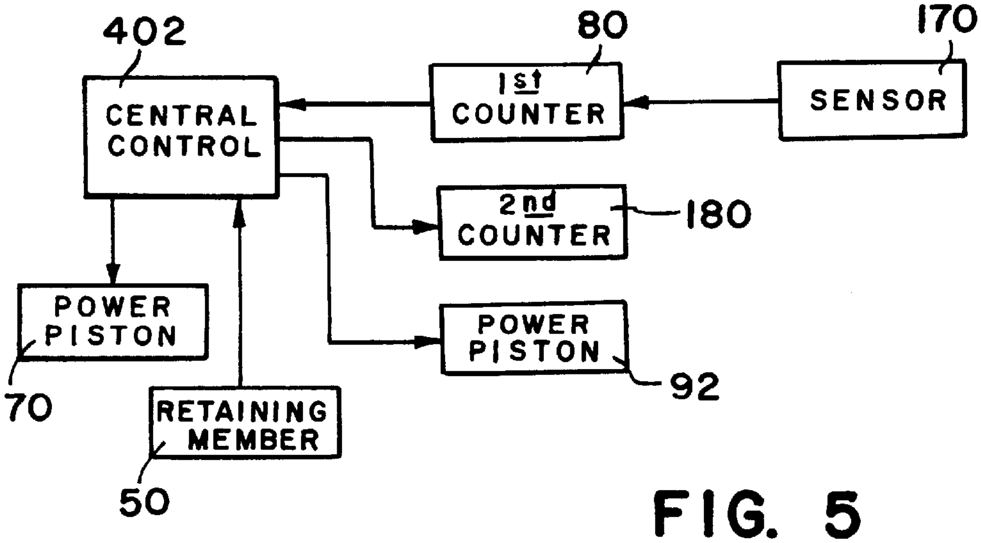
FIG. 5 is a schematic illustration of the operational relationship of the central control center and various components in the debeaker system of FIG. 1.

A projection 71 extends from driver mechanism 70 and provides a proximity sensor 170, of a type sold by Turck Inc. under Model No. N: 15-G30-AX3X, with a signal each time that cutting device 72 engages a bird. The debeaker apparatus 14 as best shown in FIG. 4 is designed to accommodate two birds with each downward movement of driver piston 70 and as a result the signal provided by sensor 170 represents the debeaking of two birds. The first counter 80 is programmed to account for the two birds such that an accurate number of birds that have been debeaked is displayed in window 82' and so that the central control 402 may provided the second counter 180 so the an accurate number is registered in the first output indicator 84 and second output indicator 86.

The containment means 60 which limits the movement of a bird on release from the retaining member 50 has a shield 600 which is held between first 602 and second 604 arms. Shield 600 has a window 606 for at least viewing a bird when held in the retaining member 50. An air ramp power piston or cylinder 608 which receives an operational input from a power source (compressed air) is connected to arm 602. The power source for piston or cylinder 608 is controlled by the control center 402 for the debeaker apparatus 14. An internal spring 610 located in power piston 608 acts on arm 602 to urge shield 600 toward opening 20' in the top of chute 20. On initial actuation of the debeaking apparatus 14, the control center 402 coordinates the actuation of piston or cylinder 608 to provide a force which causes arm 602 and 604 to pivot on pins 601,601' and move shield 600 away from the top of opening 20' to an up position. With shield 600 in the up position, an operator places a bird in the retention member 50. Once a bird is accepted by the retention member 50, the control center 402 terminates air pressure to air ramp piston 608 and internal spring 610 acts on arm 602 to moves the shield 600 adjacent opening 20' of chute 20. After a bird is released from the retention member 50 power is again supplied to piston 608 and shield 600 is moved to the open position as shown in FIG. 4. The central control 402 delays the supply of air pressure to air ramp piston 608 for a predetermined time period after a bird is released from retention member 50 to assure that the bird has sufficient time to drop into chute 20.

Figure 2:
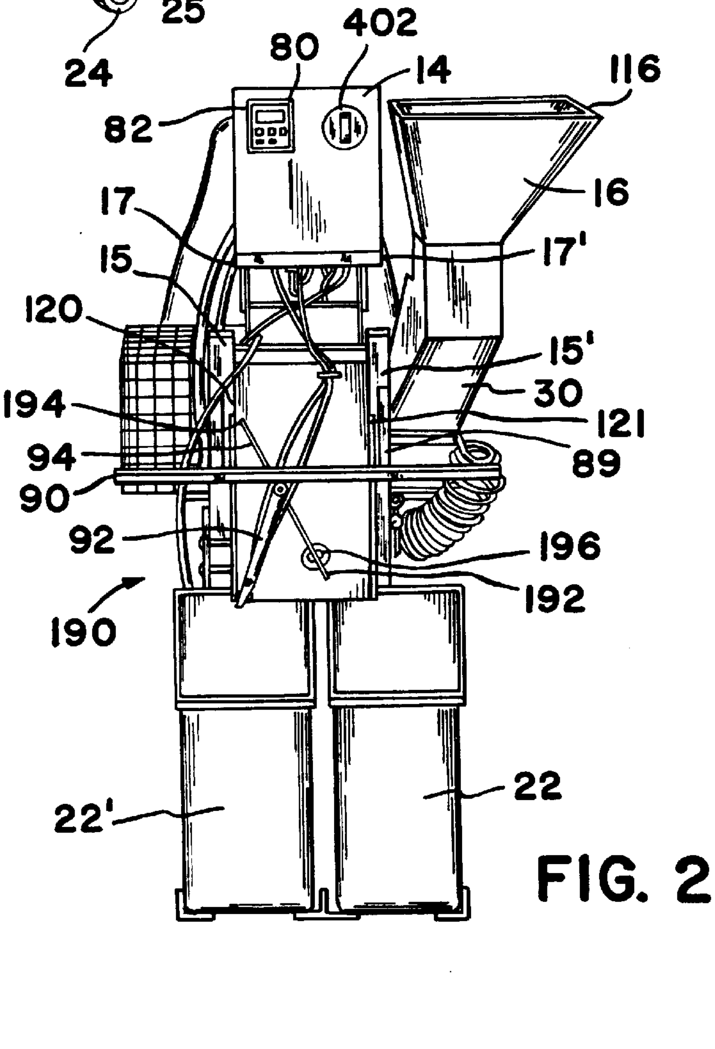
FIG. 2 is a frontal view of the system of FIG. 1 which includes a debeaking apparatus aligned with a return chute for the delivery of a bird to a storage basket.

The diverter means 190 in addition to air ramp piston or cylinder 92 has a gate 94 located in chute 20 with a first end 192 and a second end 194. The first end of gate 94 is connected to a shaft 196 located in approximately the center of chute 20 while the second end is designed to pivot about shaft 196. Cylinder 92 has a first end connected to chute 20 and a second end connected to gate 94. Cylinder 92 is designed to receive pressurized air from the power supply of the debeaker apparatus 14 as directed by central control 402 responding to a signal from the first counter 80 and the input programmed therein relating to the predetermined number of birds desired to be supplied to a storage basket 22,22'. When pressurized air is supplied to cylinder 92 an internal spring is overcome and the piston expands to cause the second end of gate 94 to pivot on shaft 196 and engage either a first side 120 as shown in FIG. 2 or a second side 121 and direct a predetermined birds into a storage basket 22. For some applications, it may be desirable to replace air ramp piston or cylinder 92 with a solenoid or to move gate 94 with a rotary torque applied to shaft 196.

The staging means 218 which includes the orientation or staging cage 18 has sides 220 and top section 221 made from a mesh material and platform 40 made from a solid member. The front edge 240 of platform 40 is lower that the rear edge 242 such that a slanted surface is created with the rear edge 242 has a higher elevation that the front edge 240. In some instances, it may also be desirable to provide an additional slant for platform 40 such that birds slide from the entrance of chute 16 toward edge 244 of staging cage 18. The top section 221 has an opening 248 for receiving return chute 20 while opening 44 in the front side 260 of the staging cage 18 is located adjacent the top section 221 so that birds with be provided with an enclosure but an operator to may freely reach into the staging cage 18 and remove a bird for presentation to retention member 50.

A seat means 400 is an air ride type and located on base 13. Seat has a position adjustment feature such that an operator may sit but be able to move with respect to the orientation cage 18 as an operator may be more comfortable by changing position after a period of time.

Mode of Operation of the Invention

The debeaking system 10 is placed into operation by a first operator moving truck or frame apparatus 12 close to a starter cage. The first operator resets the first input for the first counter 80 with a desired number for birds to be placed in storage baskets 22,22'. Most often an operator also resets the second counter 180 so that the first output indicator 84 at zero provide a sub-total of the operation of the debeaker apparatus 14 within a particular barn. Thereafter, a plurality of birds are obtained from a starter cage and placed in opening 116 of receiving chute 16. Surface 30 in receiving chute 16 is slanted and as a result the birds slide into orientation cage 18 with its slanted platform 40. The slanted platform 40 induces the birds to be oriented in a direction facing away from an operator and toward a front side 260. With birds located in the staging cage 18, a second operator, who is designed to be seated on seat 400, provides the central control 402 with an initial input to start the debeaker apparatus 14. The initial input for the debeaker apparatus 14 allows operational pressurized air flow to air ramp piston 608 and move arm 602 about pivot 601 to cause shield 600 to move to the opened position as shown in FIGS. 3 and 4. With shield 600 in an up position, an operator reaches into the orientation cage 18 and grabs a first bird which is placed into a first retaining means 50 and thereafter grabs a second bird which is placed into a second retaining means 50' of the debeaker apparatus 14. Once the first and second retaining members 50,50' accept the birds, the birds are brought into a position as illustrated in FIG. 3. When the birds are accepted by the first and second retaining members 50,50', switch 404 is activated such that the central control 402 terminates the supply of pressurized air supplied to air ramp piston 608 to allow internal spring 610 to act on arm 602 to bring shield 600 to a closed position adjacent opening 20' of chute 20 and initiate the communication of pressurized air to air ramp power piston 70 to move cutter 72 such that a portion of the beak of a bird is removed. As projection 71 attached to power piston 70 approaches sensor 170 a signal is provided to the first counter 80 corresponding to the operation of the cutter 72. This signal represents a count and is retained in counter mechanism 80.

When cutter 72 has moved to a position to remove a portion of the beak, the supply of pressurized to air ramp power piston 70 is terminated and a spring associated therewith returns the power piston 70 to its up position as illustrated in FIG. 3. Thereafter, retainer members 50,50' releases the birds into return chute 20. After a predetermined time period passed sufficient for a bird to drop into chute 20, the central control 402 operates a control such that pressurized air supplied power is again provided to air ramp piston 608. When air ramp piston 608 is supplied with pressurized air, arms 602 and 604 move shield 600 to the up position to allow an operator to again present birds to the retention members 50,50' to and begin another cycle of the debeaker system.

Cycling of the debeaker apparatus 14 continues until the predetermined number of birds programmed in the first counter 80 have been debeaked. When this number is achieved, central control 402 operates a valve such that pressurized air is supplied to air ramp piston or cylinder 92 to move gate 94 against side wall 121 and divert birds to storage basket 22'. Once a storage basket 22 has received a desired number of birds, the first operator may remove the storage basket from base 13 and return the now debeaked birds to a growing cage.

The debeaking system 10 disclosed herein reduces the time and labor involved in debeaking a flock of bird by bringing a debeaker apparatus 14 to a bird house and essentially eliminates trauma induced in the birds associated with the transportation of birds from a starter cage to a debeaking apparatus and back to a growing cage.

I claim:

1. In a system for disabling a beak of a bird, said system having retaining means for positioning the head of the bird at a location whereby a debeaking apparatus engages its beak and removes at least a portion thereof, the improvement comprising:

staging means connected to a housing for holding a plurality of birds from which an operator selects said bird and places its head into said retaining means;

control means for controlling the operation of said debeaking apparatus and for the release of said bird from said retaining means after removal of said portion of its beak;

containment means associated with said debeaking apparatus for limiting a direction of movement of said bird on release from said retaining means;

first chute means secured to said housing and aligned with said debeaking apparatus for receiving said bird on release from said retaining means, said first chute delivering said bird to one of first and second storage baskets;

counter means for totaling a number of birds engaged by said debeaking apparatus;

diverter means responsive to a signal derived from said counter means and connected to said first chute means for directing a predetermined number of birds to each of said first and second storage baskets; and means associated with said housing for moving said system from one location to another location.

2. The system as recited in claim 1 wherein said staging means includes:

an orientation cage connected to said housing and having a platform, said platform having a front edge and a rear edge, said rear edge having a higher elevation than said front edge to create an inclined surface on which said plurality of birds stand such that the plurality of birds have a tendency to face said rear edge.

3. The system as recited in claim 2 wherein said staging means further includes:

second chute means attached to housing and connected to said orientation cage for receiving said plurality of birds from an operator and for directing said plurality of birds to said platform.

4. The system as recited in claim 3 wherein said containment means includes:

a shield held between first and second arms and covering a top portion of said first chute, said shield having a window for at least viewing said bird and said retaining means; and means for pivoting said first and second arms to move said shield from a closed position to an opened position and allow the operator to present a bird from said orientation cage to said retaining means.

5. The system as recited in claim 4 wherein said means for pivoting means includes:

a first power piston connected to receive an operational input from with control means for moving said shield to said opened position, said movement to said opened position being delayed for a predetermined time after said bird is released from said retaining means; and resilient means for moving said shield to said closed position after an operator presents a bird to said retaining means.

6. The system as recited in claim 5 wherein said counter means includes:

a first counter for providing said diverter means with an operational signal corresponding to a desired number of birds for retention in said first and second storage baskets;

a second counter having a first read out for providing an operator with a total number of birds debeaked during a fixed time period of operation of said debeaking apparatus and a second read out for providing an operator with a serial total of the number birds debeaked by said debeaking apparatus.

7. The system as recited in claim 6 wherein said diverter means includes:

a gate having a first end and a second end; and a shaft aligned within said first chute and connected to said gate adjacent said first end, said shaft allowing said second end of said gate to be moved into a positioned to direct birds into a desired storage basket.

8. The system as recited in claim 7 wherein said means for moving said housing includes:

wheels attached to a frame; and a bar attached to said frame to allow an operator to apply a force for moving said system from one location to a second location.

9. The system as recited in claim 8 wherein each of said first and second storage baskets include:

a base having vertical side walls with one side wall being outwardly slanted from said base to a top surface of the basket, said slanted wall allowing an operator to return birds retained in the storage basked to a growing cage by sliding on said slanted wall.

10. The system as recited in claim 8 further including:

seat means located on said frame, said seat means being adjustable for positioning an operator adjacent said orientation cage.

* * * * *